US009442116B2

(12) United States Patent
Lancaster

(10) Patent No.: US 9,442,116 B2
(45) Date of Patent: Sep. 13, 2016

(54) METHOD OF PREDICTING CHEMOTHERAPEUTIC RESPONSIVENESS OF CANCER

(75) Inventor: Johnathan M. Lancaster, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 12/765,995

(22) Filed: Apr. 23, 2010

(65) Prior Publication Data

US 2010/0292087 A1 Nov. 18, 2010

Related U.S. Application Data

(63) Continuation of application No. PCT/US2008/080939, filed on Oct. 23, 2009.

(60) Provisional application No. 60/981,963, filed on Oct. 23, 2007.

(51) Int. Cl.
*C40B 30/02* (2006.01)
*G01N 33/574* (2006.01)
*G01N 33/50* (2006.01)

(52) U.S. Cl.
CPC .... *G01N 33/57449* (2013.01); *G01N 33/5023* (2013.01); *G01N 2800/44* (2013.01)

(58) Field of Classification Search
USPC .................................................. 435/6; 702/19
See application file for complete search history.

(56) References Cited

U.S. PATENT DOCUMENTS

2003/0225528 A1* 12/2003 Baker et al. .................... 702/19
2006/0154250 A1 7/2006 Morris et al.
2007/0172844 A1 7/2007 Lancaster et al.

OTHER PUBLICATIONS

West et al.; Predicting the clinical status of human breast cancer by using gene expression profiles; PNAS; vol. 98, No. 20, 11462-11467; Sep. 25, 2001.*
Affimetrix GeneChip Human Genome U133 2.0 Arrays FAQ; http://www.affymetrix.com/support/help/faqs/hgu133_2/faq_7.jsp; accessed Jul. 13, 2012.*
Dressman et al.; Retraction of the article "An Integrated Genomic-Based Approach to Individualized Treatment of Patients With Advanced-Stage Ovarian Cancer"; J Clin Oncol 25:517-525, 2007; published Jan. 27, 2012.*
Fox et al. 1985. "Formaldehyde Fixation." J. Histochem. Cytochem. vol. 33. No. 8. pp. 845-853.
Kunkel et al. 1981. "Contact-Site Cross-Linking Agents." Mol. Cell. Biochem. vol. 34. pp. 3-13.
Dubeau et al. 1986. "Southern Blot Analysis of DNA Extracted From Formalin-Fixed Pathology Specimens." Cancer Research. vol. 46. pp. 2964-2969.
Shi et al. 1991. "Antigen Retrieval in Formalin-Fixed, Paraffin-Embedded Tissues: an Enhancement Method for Immunohistochemical Staining Based on Microwave Oven Heating of Tissue Sections." J. Histochem Cytochem. vol. 39. No. 6. pp. 741-748.
Shedden et al. 2008. "Gene Expression-Based Survival Prediction in Lung Adenocarcinoma: a Multi-Site, Blinded Validation Study." Nat. Med. vol. 14. No. 8. pp. 822-827.
Collet et al. 1994. "The Identification of Nuclear and Mitochondrial Genes by Sequencing Randomly Chosen Clones from a Marsupial Mammary Gland cDNA Library." Biochem Genet. vol. 32. Nos. 5/6. pp. 181-190.
Aviel-Ronen et al. 2006. "Large Fragment Bst DNA Polymerase for Whole Genome Amplification of DNA From Formalin-Fixed Paraffin-Embedded Tissues." BMC Genomics. vol. 7. No. 312. pp. 1-10.
Shi et al. 2002. DNA Extraction from Archival Formalin-Fixed, Paraffin-Embedded Tissue Sections Based on the Antigen Retrieval Principle: Heating Under the Influence of pH. The Journal of Histochemistry & Cytochemistry. vol. 50. No. 8. pp. 1005-1011.
Hood et al. 2006. "Unravelling the Proteome of Formalin-Fixed Paraffin-Embedded Tissue." Briefings in Functional Genomics and Proteomics. vol. 5. No. 2. pp. 169-175.
Cook et al. 2000. "Binary Response and Logistic Regression Analysis." Part of the Iowa State University NSF/ILI Project Beyond Traditional Statistical Methods. http://www.faculty.sbc.edu/bkirk/Biostatistics/course%20documents%20for%202006/Logistic%20Regression%20Analysis.doc.
Dressman et al. 2007. "An Integrated Genomic-Based Approach to Individualized Treatment of Patients with Advanced-Stage Ovarian Cancer" Journal of Clinical Oncology. vol. 25. No. 5. pp. 517-525.
Nugen Technologies, Inc. 2007. "RNA Sample Quality Assessment Test for the WT-Ovation FFPE System." www.nugenine.com.
Nugen Technologies, Inc. "WT-Ovation FFPE RNA Amplification System V2." www.nugenine.com. User Guide. Catalog # 3400-12, 3400-60. Version 05.09.08. pp. i-18.
Roche. 2008. "High Pure RNA Paraffin Kit." www.roche-applied-science.com. Cat. No. 03 270 289 001. pp. 1-24.
Crockett et al. 2005. "Identification of Proteins From Formalin-Fixed Paraffin-Embedded Cells by LC-MS/MS." Laboratory Investigation. vol. 85. pp. 1405-1415.
International Search Report for PCT/US20081/080939 dated Jan. 5, 2009.

(Continued)

*Primary Examiner* — Antonio Galisteo Gonzalez
(74) *Attorney, Agent, or Firm* — Robert J. Varkonyi; Smith & Hopen, P.A.

(57) ABSTRACT

Disclosed is a method of predicting clinical tumor outcome by providing gene expression from a tumor sample. The method utilizes a novel genetic screen to identify genes that contribute to chemotherapeutic responsiveness, using formalin fixed paraffin embedded clinical samples of epithelial cancer, specifically serous ovarian cancer. The method is useful in predicting tumor responsiveness to chemotherapeutics, including alkylating agents, cisplatin, antimetabolites, plant alkaloids, and antitumor antibiotics. A microarray screen showed formalin fixed paraffin embedded samples can identify genes related to chemotherapeutic response with 86% efficiency.

13 Claims, 1 Drawing Sheet

(56) References Cited

OTHER PUBLICATIONS

Affymetrix, Inc., Apr. 2003; Data Sheet: GeneChip Human Genome Arrays; p. 2 for "human datasheet".

Genome Reference Consortium Feb. 2009; GeneChip Human Genome U133 Plus 2.0 Array for "gene sequence source" doc.
Affymetrix, Inc., Aug. 20, 2008; HG-U133_Plus_2 Probe Sequences, FATSA for the text file.

* cited by examiner

| weight 115 probes | 115 probes | weight 115 probes | 115 probes | weight 115 probes | 115 probes |
|---|---|---|---|---|---|
| 0.088126 | 241797_at | 0.038312 | 243303_at | -0.024434 | 209318_x_at |
| 0.084467 | 1560342_at | 0.037674 | 225215_s_at | -0.02381 | 208628_s_at |
| 0.082193 | 235411_at | -0.037669 | 225351_at | -0.02381 | 229776_at |
| 0.074582 | 209423_s_at | -0.037314 | 223312_at | -0.023449 | 239215_at |
| 0.071843 | 237237_at | -0.036646 | 202318_s_at | -0.022777 | 223991_s_at |
| 0.07029 | 230853_at | -0.036289 | 213482_at | -0.021446 | 216042_at |
| -0.069006 | 202129_s_at | -0.036221 | 40829_at | -0.02108 | 1554958_at |
| 0.06688 | 239504_at | -0.036075 | 1566145_s_at | -0.021068 | 229423_at |
| 0.06232 | 214759_at | -0.035973 | 224878_at | -0.02033 | 225046_at |
| 0.060026 | 236207_at | -0.035451 | 209055_s_at | -0.020297 | 220240_s_at |
| 0.059493 | 239784_at | 0.034685 | 218345_at | -0.019558 | 222458_s_at |
| 0.059488 | 225355_at | 0.034374 | 234317_s_at | -0.018434 | 230434_at |
| 0.05915 | 208530_s_at | -0.034023 | 208580_x_at | 0.017723 | 1566146_x_at |
| 0.058835 | 212170_at | -0.033858 | 203144_s_at | -0.017538 | 222029_x_at |
| 0.058817 | 225062_at | -0.033197 | 238127_at | -0.015888 | 214005_at |
| 0.056911 | 213478_at | 0.031736 | 243637_at | 0.015671 | 1568920_at |
| 0.05626 | 209615_s_at | -0.031494 | 242918_at | 0.015263 | 219341_at |
| -0.056133 | 227005_at | 0.031379 | 228341_at | 0.012863 | 220684_at |
| -0.055894 | 204243_at | -0.031154 | 221951_at | -0.011934 | 1570318_at |
| 0.055654 | 208777_s_at | -0.030851 | 241150_at | -0.011661 | 1560932_at |
| -0.055216 | 229528_at | -0.030783 | 232379_at | -0.00868 | 203346_s_at |
| 0.053579 | 226793_at | -0.030753 | 230283_at | -0.005512 | 217659_at |
| 0.050939 | 1555841_at | -0.030404 | 231222_at | 0.004061 | 215955_x_at |
| -0.050938 | 235200_at | -0.030387 | 211876_x_at | | |
| -0.05035 | 202613_at | -0.030286 | 201007_at | | |
| 0.049972 | 239136_at | 0.030221 | 1552977_a_at | | |
| 0.049901 | 1566144_at | 0.02964 | 1560846_at | | |
| 0.049658 | 234883_x_at | -0.02959 | 226500_at | | |
| -0.048841 | 238938_at | -0.029233 | 208619_at | | |
| 0.048201 | 1557918_s_at | -0.028963 | 227995_at | | |
| 0.047647 | 224015_s_at | 0.028345 | 1552760_at | | |
| 0.047051 | 233348_at | -0.027977 | 203466_at | | |
| 0.046457 | 219452_at | -0.027486 | 219726_at | | |
| 0.045805 | 226846_at | -0.027133 | 1553697_at | | |
| -0.04505 | 230855_at | -0.027043 | 216272_x_at | | |
| 0.044107 | 234955_at | -0.026859 | 226384_at | | |
| -0.044045 | 209081_s_at | -0.0265 | 218341_at | | |
| 0.043847 | 243752_s_at | 0.026366 | 214908_s_at | | |
| 0.043579 | 207550_at | -0.026211 | 206638_at | | |
| 0.042888 | 231885_at | -0.026183 | 237789_at | | |
| 0.041608 | 222347_at | -0.026095 | 1562116_at | | |
| 0.041285 | 1559559_at | 0.025924 | 206184_at | | |
| 0.041079 | 202266_at | 0.025661 | 1553212_at | | |
| -0.040419 | 220913_at | 0.025633 | 227414_at | | |
| -0.039943 | 227043_at | -0.025596 | 237003_at | | |
| 0.039046 | 213872_at | 0.025372 | 219686_at | | |

METHOD OF PREDICTING CHEMOTHERAPEUTIC RESPONSIVENESS OF CANCER

CROSS REFERENCE TO RELATED APPLICATIONS

This application is a continuation of prior filed International Application, Serial Number PCT/US2008/080939 filed Oct. 23, 2008, which claims priority to U.S. provisional patent application No. 60/981,963 filed Oct. 23, 2007 which is hereby incorporated by reference into this disclosure.

STATEMENT OF GOVERNMENT INTEREST

This invention was made with Government support under Grant No. DAMD17-02-2-0051 awarded by the Department of Defense. The Government has certain rights in the invention

FIELD OF INVENTION

This invention relates to cancer diagnosis methods. Specifically, the invention is a method of determining the response of a cancer to chemotherapy using gene expressions of formalin-fixed paraffin embedded tissue samples.

BACKGROUND OF THE INVENTION

A cornerstone of personalized cancer care will be the ability to predict how an individual patient will respond to a therapeutic intervention. Recent reports suggest that gene expression profiles have the potential to discriminate between patients who will and will not respond to specific chemotherapeutic agents. However, most existing gene expression predictive signatures have been developed and tested in fresh-frozen (FF) tissues and their utility in formalin fixed paraffin embedded (FFPE) samples, commonly encountered in clinical practice, is unknown.

Formalin fixation and wax embedding is a universal tissue processing procedure, allowing samples to be cut into thin sections (i.e. a few microns) stored at room temperatures indefinitely. Formalin-fixed paraffin-embedded (FFPE) archival clinical specimens are invaluable in discovery of prognostic and therapeutic targets for diseases such as cancer. Acquisition of appropriate clinical samples remains a fundamental problem in diagnosis. Tissue biopsies are difficult to obtain and therefore are too valuable to be used in global diagnosis development in most instances. A vast archive of tissue samples exists for every conceivable condition as formalin-fixed (FF) and paraffin-embedded (PE) samples. FFPE samples are prepared by incubating the tissue in a buffered formalin solution of 3.7% (w/v) formaldehyde and 10-15% methanol, forming intra- and intermolecular covalent crosslinks between proteins, RNA and DNA (Fox, C. H., et al., Formaldehyde fixation. *J. Histochem. Cytochem.* 1985; 33:845-53; Kunkel, G. R., et al., Contact-site cross-linking agents. *Mol. Cell. Biochem.* 1981; 34:3-13). Afterwards, the samples are embedded with paraffin, which enables FFPE samples have been used to diagnose and stage tumors and evaluate protein expression by immunohistochemistry (IHC) and in situ hybridization.

Throughout a century of use, numerous archival paraffin-embedded tissue banks have been established worldwide. These tissue banks are invaluable resources of tissues for translational studies of cancer and various other diseases. Accessibility of macromolecules in the samples is a critical issue, as FFPE samples are traditionally limited to IHC.

Recent developments in extraction methodologies have opened FFPE samples to new analyses, like MS. An antigen retrieval (AR) technique, by boiling FFPE samples in water was shown to enhance IHC by circumventing the formalin fixation, and is now the typical approach for IHC staining of FFPE samples (Shi et al. 1991). Recently, AR and proteinase K/SDS treatment has been shown useful in extracting nucleic acids (Hood et al. 2006; Dubeau et al. 1986). These techniques rely on either strong heating of FFPE samples or enzyme digestion.

Proteomic studies of FFPE samples have been severely limited due to the formaldehyde-induced crosslinking, which renders proteins insoluble and unsuitable for biochemical extraction and analysis. For example, crosslinking prevents extraction of proteins from FFPE samples for use in protein analysis, such as Western blots. The advances in FFPE processing techniques have yet to overcome these obstacles, since many proteins are still undetectable (Crockett, D., et al., Identification of proteins from formalin-fixed paraffin-embedded cells by LC-MS/MS. *Lab. Invest.,* 2005; 85:1405-1415).

A predictor for ovarian cancer response to platinum-based therapy is needed for use with stable patient samples, such as formalin fixed paraffin embedded samples.

SUMMARY OF THE INVENTION

Disclosed is a method of predicting clinical tumor outcome by providing gene expression from a tumor sample (Shedden, K., et al., Gene expression—based survival prediction in lung adenocarcinoma: a multi-site, blinded validation study. Nat. Med. 14(8):822-7. (2008)). The gene expression may be obtained from any number of means known in the art, including without limitation, Polymerase Chain Reaction, ChIp, gene array, microarrays or quantitative-Polymerase Chain Reaction (Q-PCR), and reverse transcriptase Polymerase Chain Reaction (rt-PCR). The present method utilizes a novel genetic screen to identify genes that contribute to chemotherapeutic responsiveness, using formalin fixed paraffin embedded clinical samples. A microarray screen showed formalin fixed paraffin embedded samples can identify genes related to chemotherapeutic response with 86% efficiency. At least one threshold value is defined for classifying the gene expression levels. The extracted biological material is selected from the group consisting of DNA, RNA, protein, derivatives thereof, and fragments thereof. As used herein, derivatives refer to processed variants of DNA, RNA, or proteins, which includes, without limiting the scope of the invention, transcripts. In certain embodiments, the disclosed method uses RNA to determine gene expression. Gene expression levels are determined from the biological material in the clinical sample and compared to the gene expression of the clinical sample with a gene expression of known clinical outcome, indicative of tumor outcome. In some embodiments, the gene expression of known clinical outcome was constructed by correlating gene expression levels to clinical outcome, classifying gene expression levels by clinical outcome into gene expression groups, comparing variance between the gene expression groups, and fitting a statistical model to the gene expression groups. In specific embodiments, the statistical model is a binary regression model.

As such, disclosed is a method of predicting clinical tumor prognosis by extracting a biological material from a formalin-fixed paraffin-embedded clinical sample. Also disclosed is a method of predicting clinical tumor responsiveness to chemotherapeutic treatment from a formalin-fixed paraffin-embedded clinical sample. A method is also disclosed for predicting clinical tumor responsiveness to chemotherapeutic treatment of ovarian cancer from a formalin-fixed paraffin-embedded clinical sample. In some embodiments, the disclosed methods are useful for predicting, without limiting the scope of the invention, tumor prognosis of epithelial cancer, and in specific embodiments serous ovarian cancer. In more specific embodiments, the method is useful for predicting tumor responsiveness to chemotherapeutic treatment selected from the group consisting of alkylating agent, antimetabolite, plant alkaloid, and antitumor antibiotic. In further embodiments, the method is useful for predicting tumor responsiveness to cisplatin.

The disclosed methods utilize Polymerase Chain Reaction, ChIp, gene array, microarrays, reverse transcriptase Polymerase Chain Reaction, and quantitative-Polymerase Chain Reaction to determine gene expression in some embodiments. In certain embodiments, the methods further generated a probeset list and tested the plurality of gene expressions in the clinical sample for gene expression using the probeset list. In these embodiments, the probeset list was generated by providing a first probeset and testing the first probeset against gene expression data for a tumor cell with known chemotherapeutic outcome, wherein the gene expression data is compared to the known chemotherapeutic outcome. In some embodiments of the disclosed methods, chemotherapeutic treatment is selected from the group consisting of alkylating agent, antimetabolite, plant alkaloid, and antitumor antibiotic, and in more specific embodiments, the chemotherapeutic is cisplatin.

BRIEF DESCRIPTION OF THE DRAWINGS

For a fuller understanding of the invention, reference should be made to the following detailed description, taken in connection with the accompanying drawings, in which:

FIG. 1 is a datasheet of the 115 probe set.

DETAILED DESCRIPTION OF THE PREFERRED EMBODIMENT

"Patient" is used to describe an animal, preferably a human, to whom treatment is administered, including prophylactic treatment with the compositions of the present invention.

Disclosed is a tumor prognosis predictor based on gene expression signatures of cancer cells. Gene expression data is used to identify a patient's tumor response to chemotherapeutic intervention. The invention uses cumulative expression information from a series of genes involved in the regulation of the cell cycle and the mitotic process. This information is then used to categorize tumor samples based on the chemotherapeutic responsiveness using a mathematical model and gene expression data derived from microarrays or quantitative-Polymerase Chain Reaction (Q-PCR) data.

183 FFPE advanced stage (III/IV) serous ovarian cancers were identified, obtained during primary surgical cytoreduction from patients who went on to receive platinum-based chemotherapy. Archival formalin-fixed, paraffin-embedded tissue samples were obtained from the processed tissue as follows. Immediately after excision from the patients, samples were routinely fixed in 10% neutral buffered formalin [average period of fixation was 24 hr at room temperature (RT)]. Fixed tissues were processed routinely through dehydration in graded ethanol, clearing in xylene, and embedding in paraffin blocks using automatic processing and embedding equipment.

RNA was extracted using the High Pure RNA Paraffin Kit (Rosche Diagnostics GmbH, Mannheim, Germany). Briefly, each paraffin block was cut at 5-10 µm and xylene added for 5 min. Absolute ethanol was added to the sample and spun at 12,000×g, the supernatant removed and pellet allowed to dry. The samples were lysed using a 10% SDS/Proteinase K buffer overnight at 55° C. Proteins were precipitated using an ethanol/buffer solution and proteins collected as provided.

The extracted RNA was amplified using the WE-Ovation System (NuGen). Total RNA was measured and subjected to reverse transcriptase (RT) PCR using DNA/RNA chimeric primers. The RNA was fragmented with RNase H, forming priming sites for PCR. Amplification of the product formed double stranded cDNA and the resultant product was purified by centrifugation as provided. After amplification, the samples were loaded on an Affymetrix 133 plus 2.0 GeneChip array and analyzed.

All hybridizations were carried out at 45° C. for 16-17 h with mixing on a rotisserie at 60 rpm. Following hybridization, the solutions were removed and the arrays were rinsed with 1×MES. The arrays were washed and stained using the GeneChip Fluidics station protocol EukGE_WS2, which consists of 10 cycles of 2 mixes per cycle with non-stringent wash buffer (6×SSPE, 0.01% Tween 20) at 25° C. followed by 4 cycles of 15 mixes per cycle with stringent wash buffer (100 mM MES, 0.1 M Na+, and 0.01% Tween 20) at 50° C. The probe arrays were stained for 10 min in streptavidin-phycoerythrin solution (SAPE) [1×MES solution, 10 µg/ml SAPE (Molecular Probes, Eugene, Oreg.), and 2 µg/µl acetylated BSA (Invitrogen)] at 25° C., then washed for 10 cycles of 4 mixes per cycle at 25° C. The probe arrays were treated for 10 min with an antibody solution [1×MES solution, 2 µg/µl acetylated BSA, 0.1 µg/µl normal goat IgG (Sigma Chemical, St. Louis, Mo.), 3 µg/µl biotinylated goat-anti-streptavidin antibody, (Vector Laboratories, Burlingame, Calif.)] at 25° C. followed by a second staining for 10 min in SAPE at 25° C. The final wash was 15 cycles of 4 mixes per cycle at 30° C. with non-stringent wash buffer. The probe arrays were then scanned once at 1.56 µm resolution using the Affymetrix GeneChip Scanner 3000 or at 3 µm resolution using the Affymetrix GeneChip Scanner 2500.

Arrays were visually scanned for any defects or scanning artifacts that might compromise the final results. 87 of the younger samples were divided into a training set (n=44), with the remaining samples held out as an external validation datasets containing similar microarray data test (n=43).

Training set GeneChip results were subjected to ANOVA and Binary regression analysis to develop and test gene expression profiles associated with ovarian cancer platinum-responsiveness.

The binary regression model was provided by:

$$y_i | \pi_i = Ber(\pi_i), \pi_i = Pr(y_i = 1) = F(x_i' \beta), \quad (01)$$

(Collet, 1994), where $y_i=1$ if the response of interest is observed for the $i^{th}$, $p_i$ is the probability the $i^{th}$ individual is responsive, $\beta$ is the K vector of unknown parameters, $x_i' = (x_i, \ldots, x_{iK})$ the K vector of known covariates associated to the $i^{th}$ individual and F any transformation for 0 and 1. Thus, $$F(x_i^t \beta) = \begin{cases} \exp(x_i^t \beta)/[1 + \exp(x_i^t \beta)], & \text{(logistic)} \\ \Phi(x_i^t \beta), & \text{(probit)} \\ 1 - \exp[-\exp(x_i^t \beta)]. & \text{(complementary log-log)} \end{cases} \quad (02)$$

Thereby providing the formula, $$p(y \mid \beta) = \prod_{i=1}^{n} [F(x_i^t \beta)]^{y_i} [1 - F(x_i^t \beta)]^{(1-y_i)}. \quad (03)$$

The data underwent Bayesian analysis, making $$p(\beta \mid y) \propto p(\beta) \prod_{i=1}^{n} [F(x_i^t \beta)]^{y_i} [1 - F(x_i^t \beta)]^{(1-y_i)}. \quad (04)$$

The 115 probe set predictor, shown in FIG. 1, was used to test the patient samples. The Predictor correctly identified 27/33 (82%) platinum complete responders (CR) and 10/11 (91%) incomplete responders (IR) for an overall accuracy of 37/44 (84%) in leave-one-out cross validation. In the external validation set, the 115 probe set predictor correctly identified 26/32 (81%) CR and 9/11 (82%) IR samples, with an overall accuracy of 35/43 (81%).

Microarray expression analysis of FFPE samples identified genes that influence ovarian cancer platinum-responsiveness and is useful in predicting chemoresponsiveness in a chemo-predictive assay with clinical utility.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a tumor prognosis prediction method, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween. Now that the invention has been described.

What is claimed is:

1. A method of measuring DNA expression of genes in a formalin-fixed paraffin-embedded clinical sample, where the genes are provided in FIG. 1, comprising the steps of:
   extracting a biological material from the formalin-fixed paraffin-embedded clinical sample, wherein the biological material is RNA, further comprising:
   subjecting the formalin-fixed paraffin-embedded clinical sample to xylene;
   lysing cells in the sample with a detergent and a proteinase inhibitor solution;
   generating cDNA from the RNA, further comprising:
   fragmenting the RNA;
   subjecting the fragmented RNA to reverse transcriptase Polymerase Chain Reaction to form cDNA; and
   obtaining a plurality of nucleic acid expressions in the clinical sample further comprising:
   contacting the cDNA with a probeset to form the plurality of nucleic acid expressions, wherein the probeset is provided in FIG. 1;
   measuring the hybridization of the cDNA to the probeset to provide a measure of DNA expression of genes in a formalin-fixed paraffin-embedded clinical sample.

2. The method of claim 1, wherein the RNA is extracted from the formalin-fixed paraffin-embedded clinical sample by the steps of:
   precipitating the RNA using ethanol after the cells are lysed with the detergent and the proteinase inhibitor solution; and
   collecting the precipitated RNA;
   wherein the detergent and the proteinase inhibitor solution is made of sodium dodecyl sulfate and Proteinase K.

3. The method of claim 1, wherein the formalin-fixed paraffin-embedded clinical sample is cut into 5-10 μm slices prior to subjecting the formalin-fixed paraffin-embedded clinical sample to xylene.

4. The method of claim 1, further comprising treating the formalin-fixed paraffin-embedded clinical sample subjected to xylene with ethanol to form an ethanol-treated formalin-fixed paraffin-embedded clinical sample.

5. The method of claim 4, further comprising centrifuging the ethanol-treated formalin-fixed paraffin-embedded clinical sample.

6. The method of claim 5, wherein the ethanol-treated formalin-fixed paraffin-embedded clinical sample is centrifuged at 12,000×g.

7. The method of claim 1, wherein the detergent and proteinase inhibitor solution is 10% sodium dodecyl sulfate/Proteinase K buffer.

8. A method of measuring DNA expression in a formalin-fixed paraffin-embedded clinical sample, where the genes for the DNA expression are provided in FIG. 1, comprising the steps of:
   extracting a biological material from a formalin-fixed paraffin-embedded clinical sample, wherein the biological material is RNA, further comprising:
   subjecting the formalin-fixed paraffin-embedded clinical sample to xylene;
   lysing cells in the sample with a 10% SDS/Proteinase K buffer solution;
   generating cDNA from the RNA, further comprising:
   fragmenting the RNA;
   subjecting the fragmented RNA to reverse transcriptase Polymerase Chain Reaction to form cDNA; and
   obtaining a plurality of nucleic acid expressions in the clinical sample further comprising subjecting the biological material to a probeset, wherein the probeset is provided in FIG. 1.

9. The method of claim 8, wherein the RNA is extracted from the formalin-fixed paraffin-embedded clinical sample by the steps of:
   precipitating the RNA using ethanol after the cells are lysed with the detergent and the proteinase inhibitor solution; and
   collecting the precipitated RNA.

10. The method of claim 8, wherein the formalin-fixed paraffin-embedded clinical sample is cut into 5-10 μm slices prior to subjecting the formalin-fixed paraffin-embedded clinical sample to xylene.

11. The method of claim 8, further comprising treating the formalin-fixed paraffin-embedded clinical sample subjected to xylene with ethanol to form an ethanol-treated formalin-fixed paraffin-embedded clinical sample.

12. The method of claim 11, further comprising centrifuging the ethanol-treated formalin-fixed paraffin-embedded clinical sample.

13. The method of claim 12, wherein the ethanol-treated formalin-fixed paraffin-embedded clinical sample is centrifuged at 12,000×g.

* * * * *